(12) United States Patent
Singh et al.

(10) Patent No.: US 10,748,034 B2
(45) Date of Patent: Aug. 18, 2020

(54) METHOD AND SYSTEM FOR LEARNING TO OBTAIN MEDICAL SCANS OF PATIENTS (71) Applicant: Siemens Healthcare GmbH, Erlangen (DE)

(72) Inventors: Vivek Kumar Singh, Princeton, NJ (US); Klaus J. Kirchberg, Plainsboro, NJ (US); Kai Ma, Princeton, NJ (US); Yao-jen Chang, Princeton, NJ (US); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 171 days.

(21) Appl. No.: 15/866,504

(22) Filed: Jan. 10, 2018

(65) Prior Publication Data
US 2019/0213442 A1    Jul. 11, 2019

(51) Int. Cl.
G06K 9/62    (2006.01)
G16H 40/40   (2018.01)
G06N 3/08    (2006.01)
G06K 9/00    (2006.01)
G06T 7/593   (2017.01)
G06T 17/20   (2006.01)
A61B 6/00    (2006.01)

(52) U.S. Cl.
CPC ............. G06K 9/6256 (2013.01); A61B 6/54 (2013.01); G06K 9/00671 (2013.01); G06N 3/08 (2013.01); G06T 7/593 (2017.01); G06T 17/20 (2013.01); G16H 40/40 (2018.01); G06T 2207/10028 (2013.01); G06T 2207/20081 (2013.01); G06T 2210/61 (2013.01)

(58) Field of Classification Search
None
See application file for complete search history.

(56) References Cited

U.S. PATENT DOCUMENTS

| | | | | |
|---|---|---|---|---|
| 8,737,725 B2 * | 5/2014 | Wang | ................... | G06K 9/4614 382/159 |
| 9,524,582 B2 | 12/2016 | Ma et al. | | |
| 2002/0196141 A1 * | 12/2002 | Boone | ................... | A61G 10/04 340/540 |
| 2009/0221928 A1 * | 9/2009 | Einav | ................... | A61B 5/0484 600/544 |
| 2010/0086186 A1 * | 4/2010 | Zug | .......................... | A61F 2/46 382/131 |
| 2013/0083978 A1 * | 4/2013 | Frederick | ............... | G16H 50/70 382/128 |
| 2015/0213646 A1 * | 7/2015 | Ma | ............................ | G06T 7/50 345/420 |
| 2015/0324690 A1 * | 11/2015 | Chilimbi | .................. | G06N 3/08 706/25 |

(Continued)

OTHER PUBLICATIONS

Mnih, V. et al., "Human-level control through deep reinforcement learning" Nature, vol. 518, Feb. 26, 2015, 529-533.

(Continued)

Primary Examiner — Iman K Kholdebarin (57) ABSTRACT

A method for training a learning-based medical scanner including (a) obtaining training data from demonstrations of scanning sequences, and (b) learning the medical scanner's control policies using deep reinforcement learning framework based on the training data.

13 Claims, 7 Drawing Sheets (56) References Cited

U.S. PATENT DOCUMENTS

| | | | | |
|---|---|---|---|---|
| 2016/0306924 A1* | 10/2016 | Singh | ................ | G16H 30/20 |
| 2016/0350919 A1* | 12/2016 | Steigauf | ............ | G06T 7/0014 |
| 2017/0076438 A1 | 3/2017 | Kottenstette et al. | | |
| 2018/0233222 A1* | 8/2018 | Daley | ................ | A61B 90/37 |
| 2019/0156484 A1* | 5/2019 | Nye | ................ | G06T 7/0014 |
| 2019/0183591 A1* | 6/2019 | Johnson | ............ | A61B 1/0005 |

OTHER PUBLICATIONS

Silver, D. et al., "Mastering the game of Go with deep neural networks and tree search" Nature, vol. 529, Jan. 28, 2016, 484-489.

* cited by examiner

METHOD AND SYSTEM FOR LEARNING TO OBTAIN MEDICAL SCANS OF PATIENTS

FIELD

This disclosure relates to a method of training learning-based medical scanners to operate independently.

BACKGROUND

Existing scanners such as computed tomography (CT), positron emission tomography (PET), single-photon emission computed tomography (SPECT), magnetic resonance (MR), X-ray, and interventional scanners (such as Siemens Artis Zeego for Fluoroscopy) require a technician to operate the scanner in order to obtain high quality medical images. However, both the patient's experience as well as the quality of the images taken significantly varies from one facility to another based on his/her interaction with the operator as well as the prior experience of the operator with the scanner and its operations. The quality of patient experience from the patient's perspective is personal and subjective. For example, a young patient may look for efficiency while an older patient may look for greater care and slower step-by-step instructions at appropriate pace.

The present disclosure provides a method of training learning-based medical scanners to operate independently with standard protocol as well as ability to interact with the patient and guide him/her through the scanning process. Among other things, this would also allow the scanner to optimize its process to obtain the highest quality scan images, while making sure that the appropriate scanning guidelines are observed. The method can also be applied to interventional scans where the scanners are trained to avoid obstacles and move to the appropriate body region above the patient without interfering with the medical professionals unless necessary.

After deployment at a medical facility such as a hospital, the scanner would have the ability to adapt its interaction with the patients by observing other technicians' interaction during its initial use—the scanner will learn from the patient experiences rated as acceptable by the patient as well as avoiding interactions which are rated unfavorable/unpleasant. Over time, the scanner will learn to scan patients given the patient information, scan region and purpose of the scan. Although not necessary after the adaptation process, a healthcare professional may still assist the patient through the scanning process to provide additional comfort and cover contingencies that cannot be covered by the scanner (for example, additional support to the patient if patient feels dizzy or unwell before getting on the scanner).

SUMMARY

A method for training a learning-based medical scanner is disclosed. The method comprises: (a) obtaining training data from demonstrations of scanning sequences; and (b) learning the medical scanner's control policies using deep reinforcement learning framework based on the training data.

A method for training a learning-based medical scanner is disclosed where the method comprises: (a) generating a 3D representation of the scanner room scene in the coordinate system of the scanner; (b) modeling the scanner as a deep reinforcement learning agent; (c) obtaining a plurality of 3D end-to-end scanning sequences capturing the entire scanning workflows including the patient body region that was scanned and the list of actions performed by the scanner; (d) converting each of the 3D end-to-end scanning sequence data into a 3D scene data; (e) training the deep reinforcement learning agent model of the scanner to learn the control policies using the 3D scene data.

A method is disclosed where the method comprising: (a) receiving 3D range data of the scanner environment; (b) parsing the 3D range data into components of the scanner environment using the trained parsing frame work to fit a 3D mesh model to each component and obtaining a scene model of the scanner environment, where the scene model includes a 3D patient mesh model; and (c) training a deep learning agent to map the 3D patient mesh model and the body region to be scanned into control policies.

BRIEF DESCRIPTION OF THE DRAWINGS

FIG. 5 is a flowchart illustrating

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The operation of the learning-based medical scanner according to the present disclosure involves the following functions: sensing and acquiring the scene in the scanner's environment that includes the presence of a patient and producing a scenery data that includes the scanning target body region on the patient; determining the appropriate control policies for the medical scanner; and executing the control policies for the medical scanner and interacting with the patient.

Sensing:

The learning-based medical scanner is equipped with an appropriate sensor array such that it has the ability to sense the scanner room environment around itself as well as the relevant portions of the scene and produce scanner room environment data. The sensors can include but are not limited to cameras. The cameras are preferably 3D cameras with range (distance) sensing abilities. The cameras are deployed to provide sufficient coverage of the scene, the environment around the medical scanner. This can be accomplished using a geometric model of the scene obtained from the scanning room/operating room design plans, or data collected from ranging devices. The scanner room environment data generated by the sensors will include the scanner room scene geometry information including the positions of the components of the scanner room environment such as the scanner equipment itself, the patient bed, the patient, any medical professional such as the radiographer, etc. The sensing function need not be limited to obtaining the scanner room scene geometry information but also includes acquiring the necessary patient information, such as, the patient schedule as well as patient history data and the information on the medical scan that is required for the patient. Thus, the scanner room environment data includes the scanner room scene geometry information, as well as the patient information. The patient information comprises information that the scanner system observed directly from the patient through its sensors (i.e., the physical attributes of the patient such as the patient's physical dimensions that would be relevant for performing the intended scanning procedure) and the patient's medical history, treatment information and schedule. The scanner system is preferably connected to the medical facilities computer database and can obtain the patient's medical history and information.

Figure 7:
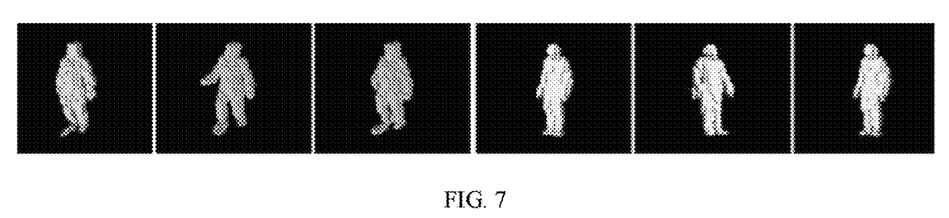
FIG. 7 shows a voxelized representation of a standing human body range surface.

Once the hardware is set up, which includes, at a minimum, the medical scanner, the patient table, and the sensor/3D camera arrays, and the devices are calibrated to each other, the relative locations of each 3D camera with respect to the scanner coordinate system is known. The 3D reconstruction of the range data from the various 3D camera devices are collected and merged into a more complete 3D reconstruction of the entire scanner room scene (visible from the camera field of view) in the scanner coordinate system. Next, this reconstruction data is converted into a voxel grid representation; a 3D occupancy grid which captures each voxel in the scene that is occupied with a physical object. For instance, FIG. 7 shows a voxelized representation of a standing human body range surface. Such a representation can be achieved using Marching cubes algorithm implemented in publicly available libraries such as VTK (Visualization ToolKit available at http://www.vtk.org/).

Figure 1:
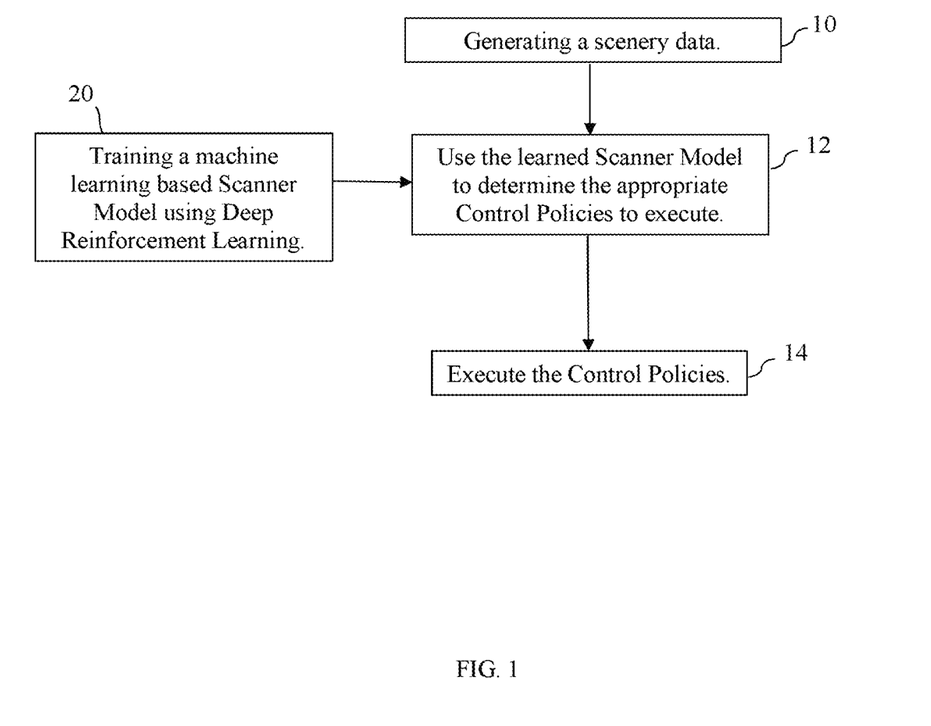
FIG. 1 is a flowchart illustrating the operational mode of a learning-based medical scanner.

Referring to the flowchart in FIG. 1, an operational mode of the learning-based medical scanner comprises generating a scenery data from the medical scanner's array of sensors. (Step 10). Taking the scenery data as an input, using a scanner model to determine the appropriate control policies for a scanning session for the patient based on the input. (Step 12). Then, having the medical scanner executing on the control policies. (Step 14).

According to an aspect of the present disclosure, the scanner model is a machine learning based model produced using deep reinforcement learning framework to learn the control policies for the medical scanner given a set of scanner room scenery data. Before the learning-based medical scanner can be operational, the scanner model is trained using deep reinforcement learning framework. (Step 20).

Figure 2:
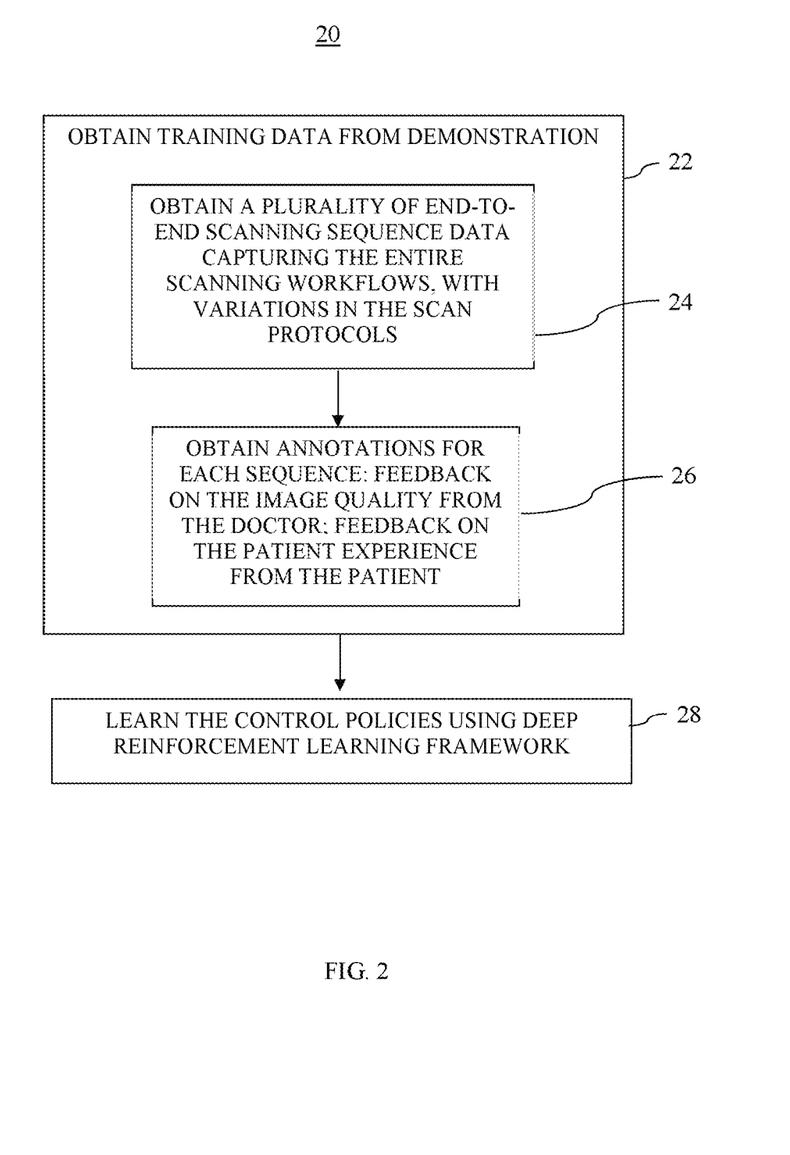
FIG. 2 is a flowchart illustrating the method of training the Scanner Model using deep reinforcement learning framework and actual demonstrations of end-to-end scanning sequences.

Learning Framework I:

Referring to FIG. 2, the training of the scanner model to operate the medical scanner based on the scenery data received from the sensors is accomplished by using deep reinforcement learning framework. In this embodiment, the medical scanner learns to operate itself based on the raw data available from the sensors by using deep reinforcement learning framework to learn the control policies given the scenery data from the sensors. The scene interpretation would be implicit in the scanner model. The deep reinforcement learning framework allows the scanner model to determine the next best action (control policy) to execute given the current input.

Machine learning frameworks such as deep reinforcement learning require a sufficient amount of appropriate training data. Referring to the process flow 20 shown in FIG. 2, in one embodiment, such training data required to train scanner model is obtained from having the medical scanner perform demonstration scanning sequences. (Step 22). This comprises obtaining a plurality of several end-to-end scanning sequence data through the sensors, capturing the entire scanning workflows, with variations in the scan protocols and patient-related parameters such as patient gender/age/shape, etc. (Step 24). Since the objective of the learning is to learn to obtain high quality scans while ensuring patient comfort, this qualitative metrics is obtained as annotations for each of the end-to-end scanning sequence data. (Step 26). In some embodiments, this can be accomplished by leveraging the existing hospital workflows for scanning data gathering. For each sequence, the feedback on the image quality would be available from the medical doctor who requested the scan and the feedback on the patient experience would be available from the patient who would be asked to rate the experience. The deep reinforcement learning framework is used to learn the control policies that will produce the desired scanning image for a patient. (Step 28).

Because reinforcement learning framework produces the optimally trained scanner model when the training involves a large number of variations in software agent's action and the resulting observed results, it is desirable to have as many of the end-to-end scanning sequence data as possible. The end-to-end scanning sequence data comprises scanner room environment data defined above.

Figure 4:
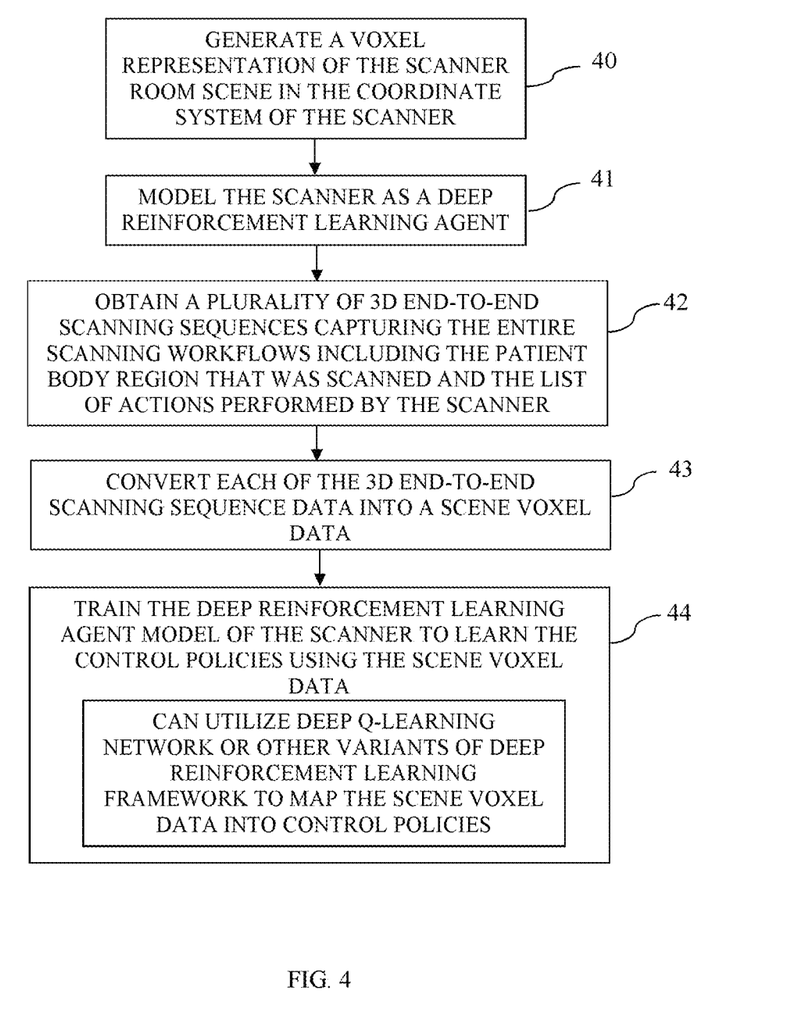
FIG. 4 is a flowchart illustrating in more detail, the method for training the Scanner Model using deep reinforcement learning framework and actual demonstrations of end-to-end scanning sequence.

Training:

Referring to FIG. 4, the learning-from-demonstrations method of training the medical scanner is described in more detail. First, a 3D representation of the scanner room scene is generated in the coordinate system of the scanner. (Step 40). Next, the medical scanner is modeled as a deep reinforcement learning agent. (Step 41). Next, a plurality of 3D end-to-end scanning sequences capturing the entire scanning workflows is obtained. (Step 42). The scanning sequences include the patient body region that was scanned and the list of actions performed by the scanner (by the radiographer). Each end-to-end scanning sequence is preferably starting from the moment the patient appears within the field of view of the cameras until the moment the patient leaves the field of view of the cameras. Following such a data acquisition effort, a dataset of several end-to-end scanning sequences of actual patient scanning will have been collected. Each of the 3D end-to-end scanning sequence data is converted into a 3D scene data. (Step 43). Then, the deep reinforcement learning agent model of the medical scanner is trained by learning the control policies using the 3D scene data. (Step 44).

Learning the control policies can be accomplished by using a deep Q-learning network to learn to map the scanner room 3D scene data into actions (the control policies). Other variants of deep reinforcement learning framework can also be used. For training the deep Q-learning network, we first initialize the weights with random values. Next, we feed the 3D scene data as input together with information on the patient body region to be scanned and the network predicted Q-value of each action that the scanner can perform (including performing no action). If the predicted action does not match the action in the training data sequence (i.e. the action that was the performed by the radiographer), we update the network weights. This training process is iterated over several patient data sequences and several hours, possibly days, until sufficient number of iterations are completed to allow the deep Q-learning agent to optimally map the scanner room 3D scene data into actions (control policies). The learned data base that includes the optimal mapping of 3D scene data to desired control policies are stored in a data storage medium of the scanner system. During operation, when a patient walks into the scanner room, the scanner controller receives a scene data as an input that includes the location and movement of the patient as well as the medical information of the patient. Then the scanner controller is prompted to access the database to determine the appropriate control policies based on the scene data input.

Figure 8:
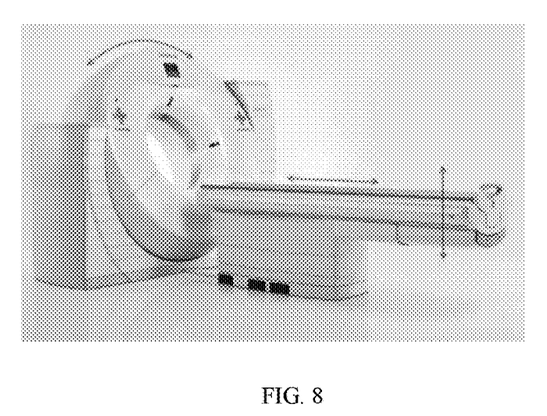
FIG. 8 shows degrees of freedom of motion for a CT scanner.
Figure 9:
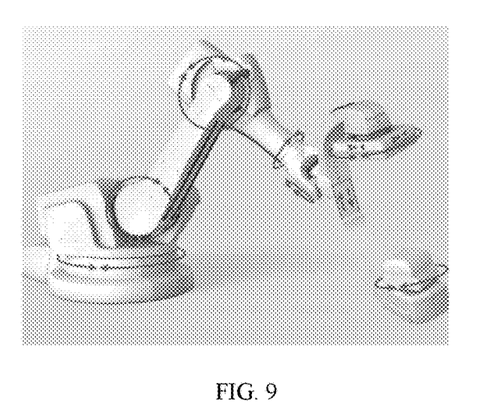
FIG. 9 shows degrees of freedom of an interventional scanner.

The control policies would include the actions that can be taken by the medical scanner taking into consideration the particular scanner's degrees of motion freedom. For instance, for CT or MR scanners, moving the patient table to an appropriate height (for patient to climb the table), positioning the patient table (to scan the appropriate region with highest quality), obtaining a topogram to refine its estimate if necessary (may be for larger or trauma patients), trigger the scan and move the table for patient unload. In operating rooms, interventional scanners such as Siemens Artis Zeego have even more degrees of freedom. The action space/degrees of freedom of the scanner control for a CT scanner and an interventional scanner (Artis Zeego) are shown in FIGS. 8 and 9, respectively. In FIGS. 8 and 9, the degrees of freedom are indicated by the arrows showing the motions allowed by each controllable and movable parts of the CT scanner and an interventional scanner (Artis Zeego).

The 3D representation of the scanner room scene and the 3D scene data can be a voxel representation, a point cloud presentation, or a geometric primitive representation. These variety of data forms for generating a 3D model representation of a scene would be well understood by those in the art.

Figure 6A:
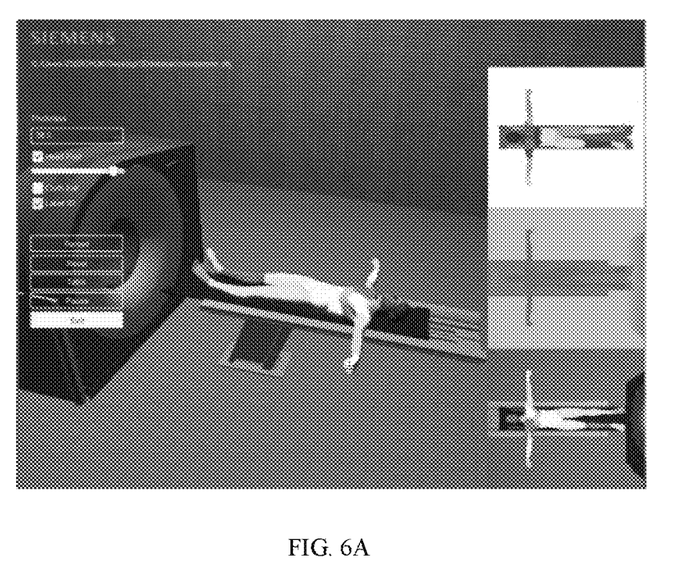
FIG. 6A shows an example of a simulated CT scanner environment.
Figure 6B:
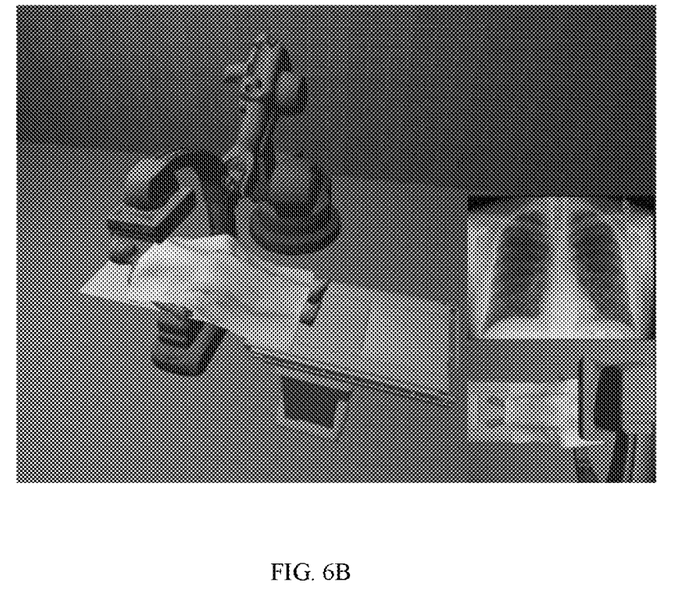
FIG. 6B shows an example of a simulated interventional scanner (Siemens Artis Zeego)

While the above described learning-from-demonstration method allows learning from a large number of actual scanning sequences, in another embodiment, one can leverage a simulation environment which can represent the scene, augmented with appropriate characters, and can simulate the scanning data acquisition process using the information obtained from scanner logs. By simulating the demonstration sequences from the actual scanner logs, we can provide even greater number of scanning sequences with a large number of variations and allow a robust learning-from-demonstration sessions. FIGS. 6A and 6B show screenshots of such simulated scenes. FIG. 6A shows an example of a simulated CT scanner environment. FIG. 6B shows an example of a simulated interventional scanner (Siemens Artis Zeego).

Figure 3:
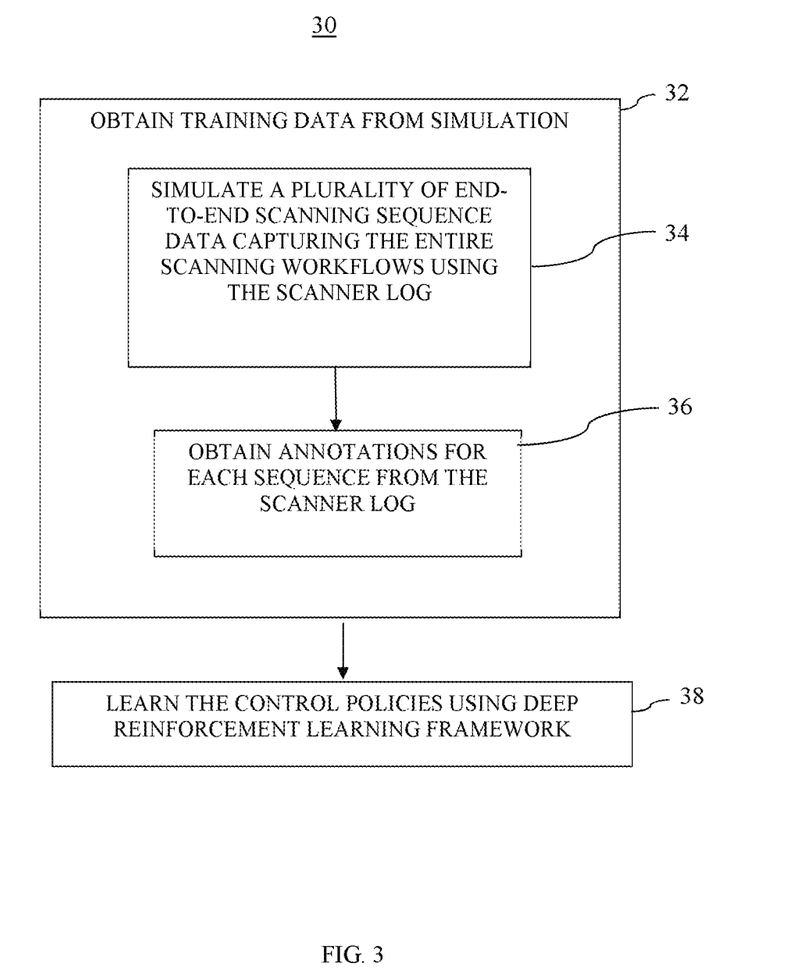
FIG. 3 is a flowchart illustrating the method of training the Scanner Model using deep reinforcement learning framework and simulated end-to-end scanning sequences simulated from the scanner log data.

Referring to the flowchart 30 in FIG. 3, the training data needed for the medical scanner to learn the Scanner Model is obtained from simulations. (Step 32). In this embodiment, the information contained in the scanner logs are used to recreate or simulate a plurality of end-to-end scanning sequence data capturing the entire scanning workflows. (Step 34). By simulating as many scanning sequences from the scanner logs as desired, sufficient variations in the scan protocols can be captured. The detailed information that are found in the scanner logs include: (a) Scanner software log including the selected scan protocol, annotated scan range in the topogram images, all user interactions, contrast type as well as amount, (b) Table logs including all events corresponding to the movement of the table as the patient is positioned (both along the gantry axis as well the height for appropriate iso-centering), as well as when the full scan is performed. The necessary annotations providing the qualitative information on the resulting scanning images can also be obtained from the scanner logs. (Step 36). The medical scanner, which is modeled as a deep reinforcement learning agent, trains itself the desired control policies that would result in an optimal scanning image given a scenery data. (Step 38). As in the embodiment where the training of the deep reinforcement learning agent is accomplished with the learning-by-demonstration method, the learned data base that includes the optimal mapping of scene voxel data to desired control policies are stored in a data storage medium of the scanner system. During operation, when a patient walks into the scanner room, the scanner controller receives a scene data as an input that includes the location and movement of the patient as well as the medical information of the patient. Then the scanner controller is prompted to access the database to determine the appropriate control policies based on the scene data input.

Scene Interpretation followed by Learning Control Policies

In another embodiment, the scanner first learns to parse the environment to obtain a "scene model" containing the frequently observed objects. This is referred to as scene understanding. This is followed by learning the control policies from the scene model. For scene understanding, the scanner is first trained to learn to parse the scene into people (patients, medical professionals) as well as other scanners or other medical equipment such as wheel chair etc. Learning the model for each of these components can be addressed using deep learning framework. The control policies from the scene model can be learned using the deep reinforcement learning method as previously explained.

Figure 5:
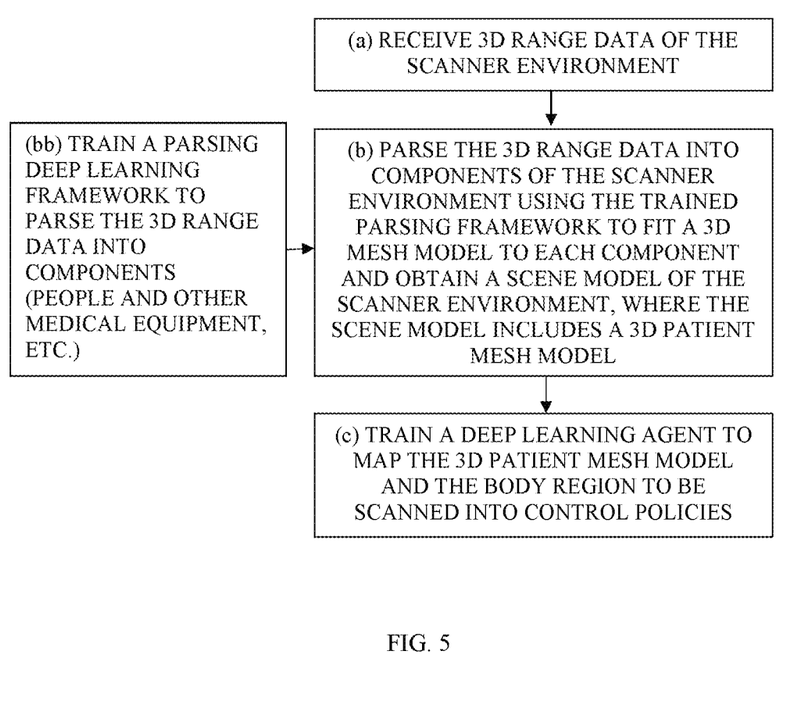

In this method, we perform the training in multiple steps. Referring to FIG. 5, in the first step, a 3D scene data of the scanner environment is received. (Step 50). Parse the 3D scene data into objects of interest such as a patient. (Step 52). This is accomplished using trained parsing framework to fit a 3D mesh model to each component and obtain a scene model of the scanner environment, where the scene model includes a 3D patient mesh model. Parsing of the 3D range data into components comprises training a parsing deep reinforcement learning framework to parse the 3D range data into components (e.g. people and other medical equipment, etc.). (Step 54). Next, a deep learning agent is trained to map the 3D patient mesh model and the body region to be scanned into control policies. (Step 56). The 3D patient mesh can be generated using the method disclosed in U.S. Pat. No. 9,524,582 to Ma et al., the disclosure of which is incorporated herein by reference. One would first parse the 3D scene and create some meshes with semantic information (such as position of the head and other body parts), and learn policies with these labeled meshes.

We detect and track the patient and fit a 3D mesh model to the patient data as the patient enters the room and gets scanned.

Given such parsing results of the objects of interest in the scene such as patient mesh, we train a deep learning agent to map the input patient mesh data as well as body region to be scanned to optimal scanner actions. The network training is done in a similar way as the first embodiment except here in a mesh for a fitted body model (which implicitly provides registration of the person across multiple frames as the patient moves).

We believe this embodiment would be easier to train since the parsing network can be trained separately, and task of the Q-network to map the registered patient mesh to optimal actions would be relatively easier. However, if we want to generalize network to take additional scene data as input, such as other scanner, a parser needs to be trained for those objects.

In yet another implementation, we could use a deep network to parse the voxel representation of the 3D scene into objects first and then use the output of this network as input to the deep Q-network to map it to optimal actions.

Here we describe an example of a workflow for a CT scanning scenario with the learned scanner operations for optimized scanning:

1. Patient enters the scanning room (may be accompanied by a healthcare professional as needed).
2. Scanner recognizes the patient based on the scanning schedule and patient medical record and matches it with the data obtained from the sensors (face). Scanner may optionally access patient history data for identification and further planning purpose. Optionally scanner greets the patient.
3. Scanner lowers the table to appropriate height based on the patient age and height and suggests the patient to lie on the table in appropriate pose necessary for the scan (head first, feet first or prone vs supine, or lateral).
4. Once the patient is stable, the scanner determines the appropriate table position required to scan the body region (based on the doctor's recommendation). If the scanner is not certain about the precise region based on cameras, it obtains a topogram scan around the required region and obtains an accurate estimate. The scanner may leverage the patient history such as metal rod in patient thigh etc.
5. Scanner now triggers the complete CT scan.
6. Once a scan is obtained, the scanner checks for the image quality at the specific region of interest.
7. Scanner moves the table to unload position and instructs the patient to unload the table and greats the patient.

Although the subject matter has been described in terms of exemplary embodiments, it is not limited thereto. Rather, the appended claims should be construed broadly, to include other variants and embodiments, which can be made by those skilled in the art. For example, one of ordinary skill in the art would understand that the inventive method described herein using CT scanner as an example can be readily applied to other X-ray scanners, PET scanners, SPECT scanners, and MR scanners, etc.

We claim:

1. A method for training a learning-based medical scanner, the method comprising:

obtaining, by the medical scanner, medical imaging data for a plurality of medical procedures;

obtaining, by an array of cameras with range sensing capabilities, a plurality of end-to-end scanning sequence data comprising scene geometry information relating to a scanner room environment during the respective plurality of medical procedures;

obtaining feedback for each of the plurality of end-to-end scanning sequence data comprising feedback on image quality for the medical imaging data received from a doctor and feedback on a patient experience received from the patient; and learning the medical scanner's control policies using a deep reinforcement learning framework and input comprising the plurality of end-to-end scanning sequence data and respective feedback.

2. The method of claim 1, wherein the end-to-end scanning sequence data comprising scene geometry information acquired using an array of sensors and patient information.

3. The method of claim 2, wherein the patient information comprises patient schedule.

4. The method of claim 3, wherein the patient information further comprises patient medical history, patient treatment information, and patient physical attributes.

5. The method of claim 1, wherein the medical scanner's control policies include actions that can be performed by the medical scanner.

6. The method of claim 1, wherein the medical scanner is a computed tomography (CT) scanner, positron emission tomography (PET) scanner, single-photon emission computed tomography (SPECT) scanner, magnetic resonance (MR) scanner, or an X-ray scanner.

7. The method of claim 1, wherein the end-to-end scanning sequence data comprises movements of a scanning table to an appropriate height and a positioning of the patient, scanning table, or patient and scanning table during a scan of an appropriate region of the patient.

8. A method for training a learning-based medical scanner, the method comprising:

(a) generating a 3D representation of a scanner room scene in a coordinate system of the scanner;

(b) modeling the medical scanner as a deep reinforcement learning agent;

(c) obtaining a plurality of 3D end-to-end scanning sequences capturing entire scanning workflows including a patient body region that was scanned and a list of actions performed by the scanner;

(d) converting each of the 3D end-to-end scanning sequences into 3D scene data; and (e) training the deep reinforcement learning agent of the medical scanner to learn control policies using the 3D scene data.

9. The method of claim 8, wherein the 3D representation of the scanner room scene and the 3D scene data comprises a voxel representation, a point cloud representation, or a geometric primitive representation.

10. The method of claim 9, wherein step (e) comprises utilizing deep Q-learning network for variants of deep reinforcement learning framework to map the 3D scene data into the control policies.

11. The method of claim 9, wherein step (b) includes learning a model for each object in the scanner room scene using a deep reinforcement learning framework.

12. A method comprising:

receiving 3D range data of a scanner environment acquired using an array of cameras with range sensing capabilities;

parsing the 3D range data into a plurality of components of the scanner environment using a trained parsing framework to fit a 3D mesh model to each component of the plurality of components;

obtaining a scene model of the scanner environment, where the scene model includes a 3D patient mesh model;

obtaining feedback for scans acquired in the scanner environment; and training a deep learning agent to map the 3D patient mesh model, the 3D mesh model, the feedback, a body region to be scanned into control policies.

13. The method of claim 12, wherein parsing comprises training a parsing deep reinforcement learning framework to parse the 3D range data into the plurality of components.

* * * * *